United States Patent
Ben Nun

(10) Patent No.: US 10,687,936 B2
(45) Date of Patent: Jun. 23, 2020

(54) HYBRID ACCOMMODATING INTRAOCULAR LENS ASSEMBLAGES

(71) Applicant: RAYNER INTRAOCULAR LENSES LIMITED, Worthing, West Sussex (GB)

(72) Inventor: Joshua Ben Nun, Beit Herut (IL)

(73) Assignee: RAYNER INTRAOCULAR LENSES LIMITED, Worthing (GB)

( * ) Notice: Subject to any disclaimer, the term of this patent is extended or adjusted under 35 U.S.C. 154(b) by 0 days.

(21) Appl. No.: 16/302,266

(22) PCT Filed: May 21, 2017

(86) PCT No.: PCT/IL2017/050566
§ 371 (c)(1),
(2) Date: Nov. 16, 2018

(87) PCT Pub. No.: WO2017/203517
PCT Pub. Date: Nov. 30, 2017

(65) Prior Publication Data
US 2019/0290422 A1    Sep. 26, 2019

(30) Foreign Application Priority Data
May 22, 2016    (IL) .......................................... 245775

(51) Int. Cl.
*A61F 2/16*    (2006.01)
(52) U.S. Cl.
CPC .......... *A61F 2/1629* (2013.01); *A61F 2/1618* (2013.01); *A61F 2/1694* (2013.01);
(Continued)

(58) Field of Classification Search
None
See application file for complete search history.

(56) References Cited

U.S. PATENT DOCUMENTS

| | | |
|---|---|---|
| 3,950,082 A | 4/1976 | Volk |
| 4,122,556 A | 10/1978 | Poler |

(Continued)

FOREIGN PATENT DOCUMENTS

| | | |
|---|---|---|
| FR | 2794965 A1 | 12/2000 |
| WO | 83/00998 A1 | 3/1983 |

(Continued)

OTHER PUBLICATIONS

Search Report—UK Application No. 1817955.6, dated Apr. 16, 2019, 6 pages.

(Continued)

*Primary Examiner* — Leslie Lopez
(74) *Attorney, Agent, or Firm* — Novick, Kim & Lee, PLLC; Harold L. Novick

(57) ABSTRACT

Hybrid Accommodating Intra Ocular Lens (AIOL) assemblages including two discrete component parts in the form of a discrete base member for initial implantation in a vacated capsular bag and a discrete lens unit for subsequent implantation in the vacated capsular bag for anchoring to the discrete base member. The lens unit includes a lens optics having at least two lens haptics radially outwardly extending therefrom. The base member includes a flat circular base member centerpiece having zero optical power.

7 Claims, 6 Drawing Sheets

(52) U.S. Cl.
CPC . *A61F 2002/169* (2015.04); *A61F 2002/1689* (2013.01); *A61F 2002/16902* (2015.04)

(56) References Cited

U.S. PATENT DOCUMENTS

| | | |
|---|---|---|
| 4,254,509 A | 3/1981 | Tennant |
| 4,298,994 A | 11/1981 | Clayman |
| 4,340,979 A | 7/1982 | Kelman |
| 4,409,690 A | 10/1983 | Gess |
| 4,409,691 A | 10/1983 | Levy |
| 4,445,998 A | 5/1984 | Kanda et al. |
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,575,374 A | 3/1986 | Anis |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,750,904 A | 6/1988 | Price, Jr. |
| 4,808,181 A | 2/1989 | Kelman |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,026,373 A | 6/1991 | Ray |
| 5,078,742 A | 1/1992 | Dahan |
| 5,171,268 A | 12/1992 | Ting et al. |
| 5,176,701 A | 1/1993 | Dusek et al. |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A | 8/1994 | Chu |
| 5,346,502 A | 9/1994 | Estabrook et al. |
| 5,476,512 A | 9/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas |
| 5,567,365 A | 10/1996 | Weinschenk et al. |
| 5,571,177 A | 11/1996 | Deacon et al. |
| 5,584,304 A | 12/1996 | Brady |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,843,188 A | 12/1998 | McDonald |
| 5,871,455 A | 2/1999 | Ueno |
| 5,895,610 A | 4/1999 | Chang |
| 5,919,230 A | 7/1999 | Sambursky |
| 5,968,094 A | 10/1999 | Werblin et al. |
| 5,984,962 A | 11/1999 | Anello |
| 6,007,579 A | 12/1999 | Lipshitz et al. |
| 6,027,531 A | 2/2000 | Tassignon |
| 6,051,024 A | 4/2000 | Cumming |
| 6,110,202 A | 8/2000 | Barraquer et al. |
| 6,117,171 A | 9/2000 | Skottun |
| 6,129,759 A | 10/2000 | Chambers |
| 6,129,760 A | 10/2000 | Fedorov et al. |
| 6,164,282 A | 12/2000 | Gwon et al. |
| 6,176,878 B1 | 1/2001 | Gwon et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,984 B1 | 9/2002 | Jalm et al. |
| 6,443,985 B1 | 9/2002 | Woods |
| 6,464,725 B2 | 10/2002 | Skotton |
| 6,488,708 B2 | 12/2002 | Sarfarazi |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,524,340 B2 | 2/2003 | Israel |
| 6,554,860 B2 | 4/2003 | Hoffmann et al. |
| 6,570,718 B2 | 5/2003 | Nomura et al. |
| 6,596,026 B1 | 7/2003 | Gross et al. |
| 6,599,317 B1 | 7/2003 | Weinschenk, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,739,722 B2 | 5/2004 | Laguette et al. |
| 6,749,634 B2 | 6/2004 | Hanna |
| 6,790,232 B1 | 9/2004 | Lang |
| 6,827,738 B2 | 12/2004 | Willis et al. |
| 6,849,091 B1 | 2/2005 | Cumming |
| 6,960,231 B2 | 11/2005 | Tran |
| 6,972,033 B2 | 12/2005 | McNicholas |
| 7,008,449 B2 | 3/2006 | Willis et al. |
| 7,025,783 B2 | 4/2006 | Brady et al. |
| 7,037,338 B2 | 5/2006 | Nagamoto |
| 7,097,660 B2 | 8/2006 | Portney |
| 7,118,597 B2 | 10/2006 | Miller et al. |
| 7,122,053 B2 | 10/2006 | Esch |
| 7,137,994 B2 | 11/2006 | De Juan, Jr. |
| 7,220,279 B2 | 5/2007 | Nun |
| 7,261,737 B2 | 8/2007 | Esch et al. |
| 7,278,739 B2 | 10/2007 | Shadduck |
| 7,350,916 B2 | 4/2008 | Hong et al. |
| 7,815,678 B2 | 10/2010 | BenNun |
| 7,842,087 B2 | 11/2010 | BenNun |
| 7,854,764 B2 | 12/2010 | BenNun |
| 7,857,850 B2 | 12/2010 | Mentak et al. |
| 7,976,520 B2 | 7/2011 | BenNun |
| 7,981,155 B2 | 7/2011 | Cumming |
| 7,998,199 B2 | 8/2011 | BenNun |
| 8,034,106 B2 | 10/2011 | Mentak et al. |
| 8,048,155 B2 | 11/2011 | Shadduck |
| 8,048,156 B2 | 11/2011 | Geraghty et al. |
| 8,057,217 B2 | 11/2011 | Graney et al. |
| 8,088,161 B2 | 1/2012 | Aharoni et al. |
| 8,273,123 B2 | 9/2012 | Ben Nun |
| 8,382,831 B2 | 2/2013 | Ben Nun |
| 8,398,709 B2 | 3/2013 | Ben Nun |
| 8,734,509 B2 | 5/2014 | Mentak et al. |
| 8,801,781 B2 | 8/2014 | Tabernero et al. |
| 8,834,565 B2 | 9/2014 | Ben Nun |
| 9,814,568 B2 | 11/2017 | Ben Nun |
| 2002/0103535 A1 | 8/2002 | Portney |
| 2003/0060881 A1 | 3/2003 | Glick et al. |
| 2003/0097177 A1 | 5/2003 | Tran |
| 2003/0204254 A1 | 10/2003 | Peng et al. |
| 2004/0073304 A1 | 4/2004 | Weinschenk, III et al. |
| 2004/0148022 A1 | 7/2004 | Eggleston |
| 2005/0107875 A1 | 5/2005 | Cumming |
| 2005/0177229 A1 | 8/2005 | Boxer Wachler |
| 2006/0069433 A1 | 3/2006 | Nun |

(56) References Cited

U.S. PATENT DOCUMENTS

| | | |
|---|---|---|
| 2006/0074487 A1 | 4/2006 | Gilg |
| 2007/0027541 A1 | 2/2007 | Aharoni et al. |
| 2007/0088433 A1 | 4/2007 | Esch et al. |
| 2007/0123981 A1 | 5/2007 | Tassignon |
| 2007/0129799 A1 | 6/2007 | Schedler |
| 2007/0129803 A1 | 6/2007 | Cumming |
| 2007/0260308 A1 | 11/2007 | Tran |
| 2007/0260309 A1 | 11/2007 | Richardson |
| 2008/0086208 A1 | 4/2008 | Nordan |
| 2008/0161914 A1 | 7/2008 | Brady et al. |
| 2009/0198247 A1 | 8/2009 | Ben Nun |
| 2010/0016965 A1* | 1/2010 | Hong ............ A61F 2/1613 623/6.34 |
| 2011/0313519 A1 | 12/2011 | Cumming |
| 2013/0116781 A1 | 5/2013 | Ben Nun |
| 2013/0304206 A1 | 11/2013 | Pallikaris et al. |
| 2014/0309734 A1 | 10/2014 | Sohn et al. |

FOREIGN PATENT DOCUMENTS

| | | |
|---|---|---|
| WO | 98/05273 A1 | 2/1998 |
| WO | 98/10717 A1 | 3/1998 |
| WO | 99/62434 A1 | 12/1999 |
| WO | 00/30566 A1 | 6/2000 |
| WO | 01/08606 A1 | 2/2001 |
| WO | 03/105669 A2 | 12/2003 |
| WO | 2008/112879 A2 | 9/2008 |
| WO | 2009/122409 A1 | 10/2009 |
| WO | 2016191614 | 12/2016 |
| WO | 2017203517 | 11/2017 |

OTHER PUBLICATIONS

Office Action—Japanese Application No. 2018-561561, dated Aug. 8, 2019, 6 pages.

* cited by examiner

HYBRID ACCOMMODATING INTRAOCULAR LENS ASSEMBLAGES

FIELD OF THE INVENTION

This invention relates to accommodating intraocular lens assemblages in general and in-the-bag accommodating intraocular lens assemblages in particular.

BACKGROUND OF THE INVENTION

Referring to FIG. 1 and FIG. 2, the structure and operation of a human eye are described as context for the present invention. FIG. 1 and FIG. 2 are cross section views of an anterior part of a human eye 10 having a visual axis VA for near vision and distance vision, respectively, in an axial plane of the human body. The human eye 10 has an anterior transparent cap like structure known as a cornea 11 connected at its circumferential periphery to a spherical exterior body made of tough connective tissue known as sclera 12 at an annular corneal limbus 13. An iris 14 inwardly extends into the human eye 10 from its root 16 at the corneal limbus 13 to divide the human eye's anterior part into an anterior chamber 17 and a posterior chamber 18. The iris 14 is a thin annular muscle structure with a central pupil. The iris 14 is activated by inter alia ambient light conditions, focusing for near vision, and other factors for a consequential change in pupil diameter. An annular ciliary body 19 is connected to zonular fibers 21 which in turn are peripherally connected to an equatorial edge of a capsular bag 22 having an anterior capsule 23 and a posterior capsule 24 and containing a natural crystalline lens 26. Contraction of the ciliary body 19 allows the lens 26 to thicken to its natural thickness T1 along the visual axis VA for greater positive optical power for near vision (see FIG. 1). Relaxation of the ciliary body 19 tensions the zonular fibers 21 which draws the capsular bag 22 radially outward as shown by arrows A for compressing the lens 26 to shorten its thickness along the visual axis VA to T2<T1 for lower positive optical power for distance vision (see FIG. 2). Near vision is defined at a distance range of between about 33 cm to 40 cm and requires an additional positive optical power of between about 3 Diopter to 2.5 Diopter over best corrected distance vision. Healthy human eyes undergo pupillary miosis to about 2 mm pupil diameter for near vision from an about 3 mm to 6 mm pupil diameter for distance vision corresponding to ambient illumination conditions.

Cataract surgery involves capsulorhexis in an anterior capsule 23 for enabling removal of a natural crystalline lens 26. Capsulorhexis typically involves preparing an about 4 mm to about 5 mm diameter circular aperture in an anterior capsule 23 to leave an annular anterior capsule flange 27 and an intact posterior capsule 24. FIG. 1 and FIG. 2 denote the boundary of the circular aperture by arrows B. Separation between a capsular bag's annular anterior capsule flange 27 and its intact posterior capsule 24 enables growth of capsular epithelial cells which naturally migrate over its internal capsule surfaces inducing opacification of a posterior capsule 24 abbreviated as PCO and/or capsular fibrosis with capsular contraction. While secondary cataracts are ruptured by YAG laser to clear a visual axis and restore vision, capsular contraction is untreatable.

Accommodating Intraocular Lens (AIOL) assemblages designed to be positioned within a vacated capsular bag 22 are known as in-the-bag AIOL assemblages. Presently envisaged in-the-bag AIOL assemblages are large monolithic dual optics structures of inherent bulkiness that require a large corneal incision for implantation in a human eye and proper positioning inside its capsular bag since a slight deviation of one optics of a dual optics structure from its visual axis results in optical distortion. Moreover, previously envisaged in-the-bag AIOL assemblages do not lend to being formed with a toric lens component for correcting astigmatism since dialing a bulky dual optics structure inside a capsular bag to a predetermined angle required to correct astigmatism poses a great risk of tearing a capsular bag.

There is a need for improved in-the-bag AIOL assemblages.

SUMMARY OF THE INVENTION

The present invention is directed towards hybrid Accommodating Intra Ocular Lens (AIOL) assemblages including two discrete component parts in the form of a discrete base member for initial implantation in a vacated capsular bag and a discrete lens unit for subsequent implantation in the vacated capsular bag for anchoring thereto. The discrete lens unit includes a lens optics having at least two lens haptics radially outwardly extending therefrom. The discrete base member includes a flat circular base member centerpiece. The lens optics and the base member centerpiece are both made of suitable implantable bio-compatible transparent optical grade material and necessarily have the same refractive index. The lens optics and the base member centerpiece are preferably made from the same material but can be made from different materials.

The lens optics has an anterior lens optics surface for distance vision correction and a posterior lens optics surface having a central circle for near vision correction. The posterior lens optics surface preferably has an annular multi-focal segment surrounding its central circle calculated for affording good intermediate vision in an implanted healthy eye. Alternatively, for implantation in an impaired vision eye, a degenerate lens unit can have a posterior lens optics surface constituted by a mono-focal lens optics surface.

The base member centerpiece has a penetration property enabling a posterior lens optics surface to be intimately immerged in its anterior base member centerpiece surface when compressed thereagainst to create a single refractive index optical continuum. Full ciliary body relaxation causes a full immersion of the posterior lens optics surface in the anterior base member centerpiece surface thereby nullifying the optical powers of both the central circle and its surrounding annular multi-focal segment such that only the anterior lens optics surface is optically active for distance vision. Ciliary body contraction causes a full axial separation of the posterior lens optics surface from the anterior base member centerpiece surface such that both the anterior lens optics surface and the posterior lens optics surface's central circle are optically active for near vision. In an intermediate ciliary body state between ciliary body contraction and full ciliary body relaxation, the posterior lens optics surface's central circle only is immersed in the anterior base member centerpiece surface, and its annular multi-focal segment is optically active together with the anterior lens optics surface for intermediate vision.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF DRAWINGS

Figure 3:
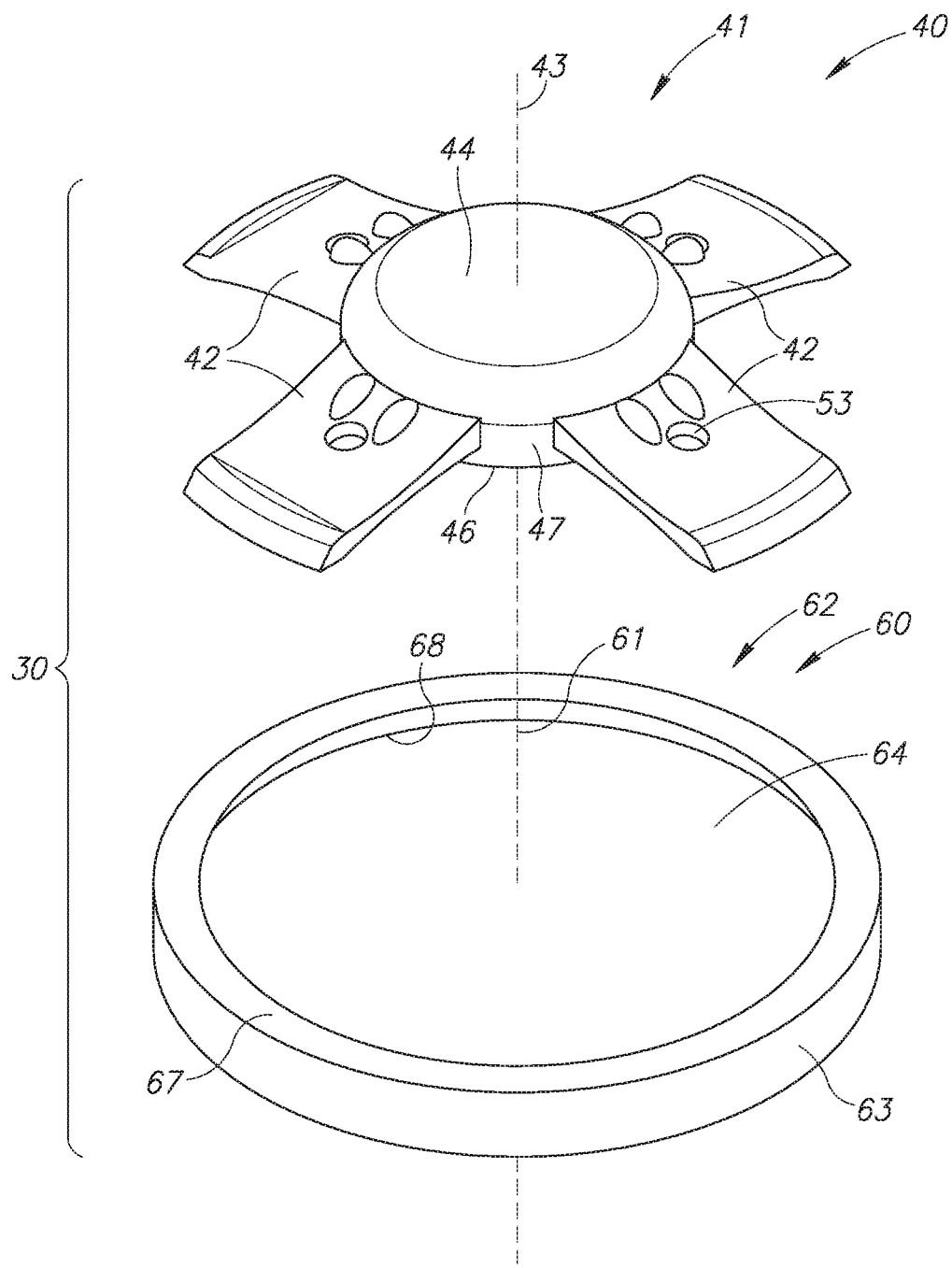
FIG. 3 is a perspective front view of a hybrid AIOL assemblage including a discrete lens unit and a discrete base member for in situ assembly in a capsular bag during cataract surgery.

FIG. 3 show a hybrid AIOL assemblage 30 including a discrete lens unit 40 and a discrete base member 60 for in situ assembly in a capsular bag during cataract surgery. The discrete lens unit 40 includes a lens optics 41 and at least two equispaced lens haptics 42 radially outward extending from the lens optics 41. The discrete lens unit 40 preferably includes four equispaced lens haptics 42. The lens unit 40 can be manufactured as a monolithic structure. Alternatively, the lens haptics 42 can be manufactured separately from the lens optics 41 and attached thereto using industry known attachment technologies. The discrete base member 60 has a base member centerline 61 and includes a flat circular base member centerpiece 62 and a base member surround 63. The base member 60 can be manufactured as a monolithic structure. Alternatively, the base member surround 63 can be manufactured separately from the base member centerpiece 62 and attached thereto using industry known attachment technologies. The hybrid AIOL assemblage 30 is entirely made from implantable biocompatible material. The lens optics 41 and the base member centerpiece 62 are made from optical grade transparent materials and have the same refractive index. The lens optics 41 and the base member centerpiece 62 are preferably formed from the same material.

Figure 4:
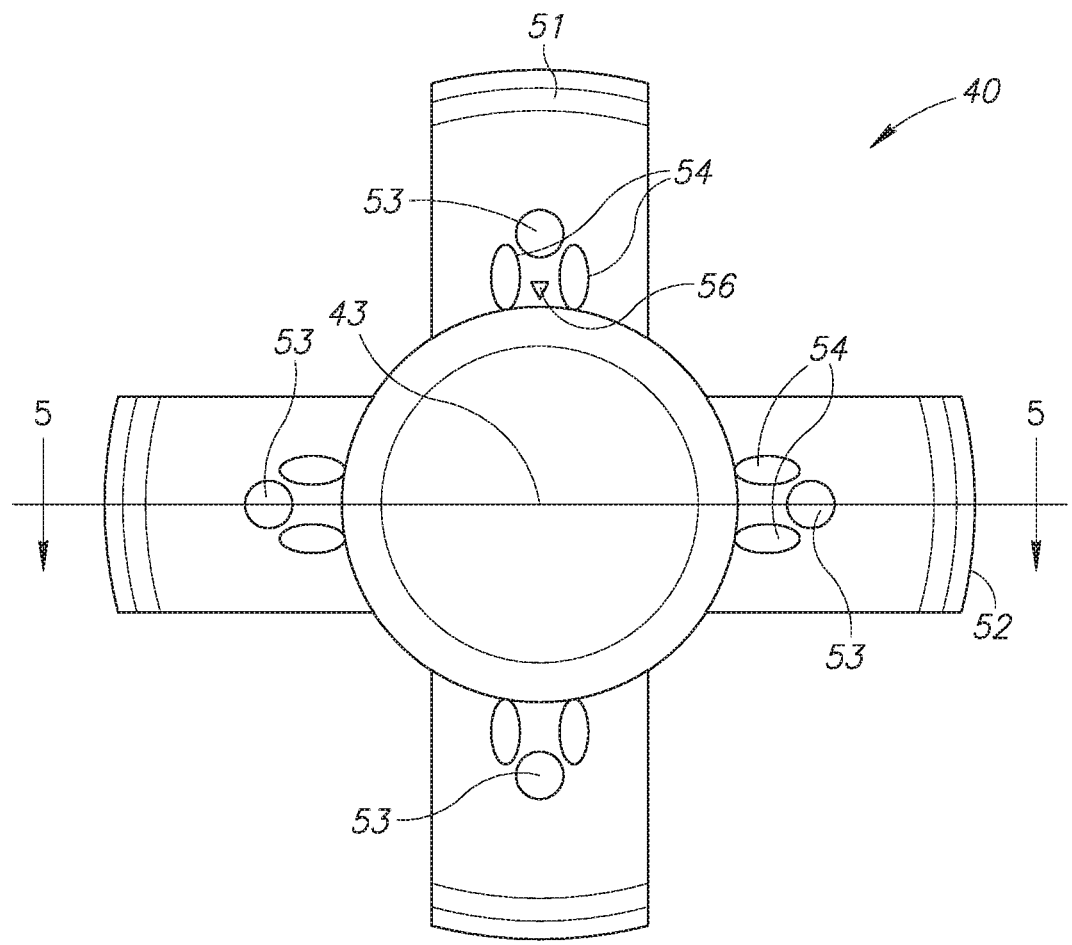
FIG. 4 is a top plan view of the discrete lens unit.
Figure 5:
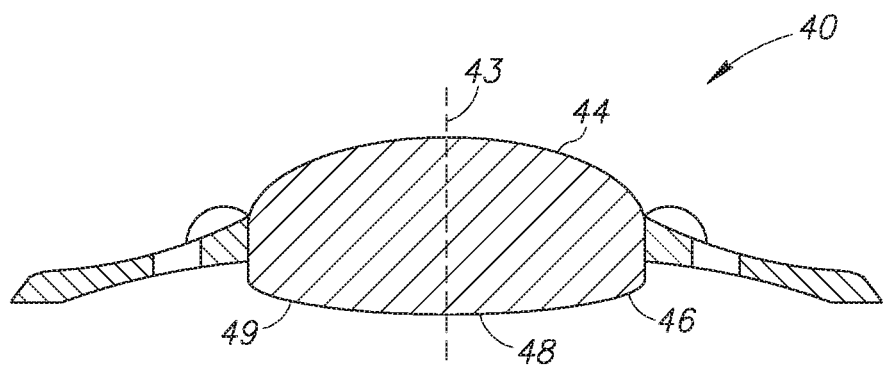
FIG. 5 is a transverse cross section of the discrete lens unit along line 5-5 in FIG. 4.

FIG. 4 and FIG. 5 show the lens optics 41 has an optical axis 43 for co-axial alignment with a visual axis VA. The lens optics 41 has an anterior lens optics surface 44, a posterior lens optics surface 46 and a lens optics edge 47. The lens optics 41 has a similar diameter and thickness as standard IOLs currently being used for cataract surgery. The anterior lens optics surface 44 affords a primary optical power calculated for optimal distance vision correction in an implanted eye. Healthy eyes require good vision at both near distance and intermediate distances and therefore the posterior optic lens surface 46 preferably has a multifocal optical gradient from a maximal optical power at the lens optics axis 43 diminishing towards the lens optics edge 47. Accordingly, the posterior lens optics surface 46 includes a center circle 48 having an approximate 2.5 mm diameter around the lens optics axis 43 corresponding to near vision pupil size under normal reading illumination conditions. The central circle 48 has the required added power to the principle distance correction optical power of the anterior lens optics surface 44 for near vision in an intended implanted eye. The central circle 48 typically has an optical power of around 3.0 Diopter. From the boundary of the central circle 48, the optical power is gradually decreased towards the lens optics edge 47 using manufacturing methods known to the art. In a degenerate version of the discrete lens unit 40 for implantation in an impaired vision eye, the posterior lens optics surface 46 can be constituted by a single mono-focal lens optics surface for providing best correction for near vision only in an intended implanted eye.

Each lens haptics 42 has a lens haptics free end 51 with a lens haptics curved edge 52 corresponding to a curvature of an anchoring interface of the discrete base member 60. Each lens haptics 42 preferably has a manipulation aperture 53 for enabling proper positioning of the lens unit 40 relative to the base member 60. Each lens haptics 42 preferably has an elongated anterior spacer pair 54 adjacent to the lens optics 41 for spacing an anterior capsule flange 27 therefrom to enable circulation of aqueous humor between an anterior capsule flange 27 and the lens unit 40.

The anterior lens optics surface 44 but can also be designed for simultaneous correction of astigmatism in an intended implanted eye. Accordingly, the lens unit 40 is provided with an optical axis marker 56 for assisting correct alignment of the lens unit 40 with respect to a human visual axis VA during implantation. The optical axis marker 56 is preferably placed on a lens haptics 42 not to impede vision. The manipulation apertures 53 are employed for dialing a properly positioned lens unit 40 around the lens optics axis 43 for setting at a required position for astigmatic correction.

Figure 6:
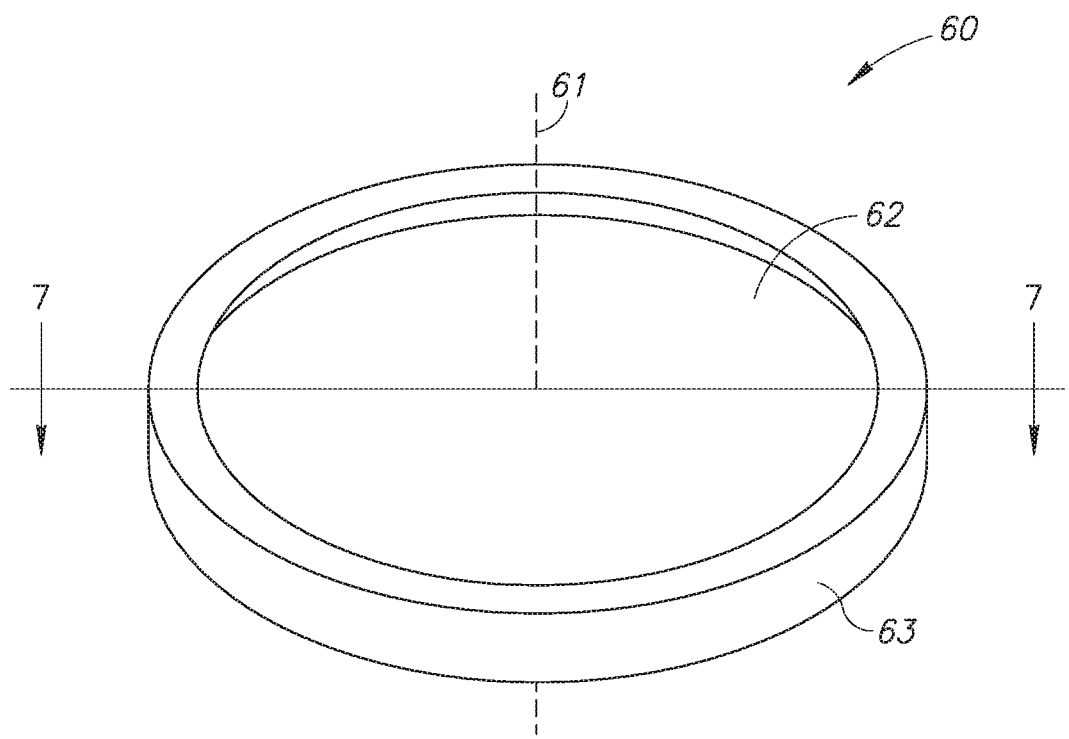
FIG. 6 is a top plan view of the discrete base member.
Figure 7:
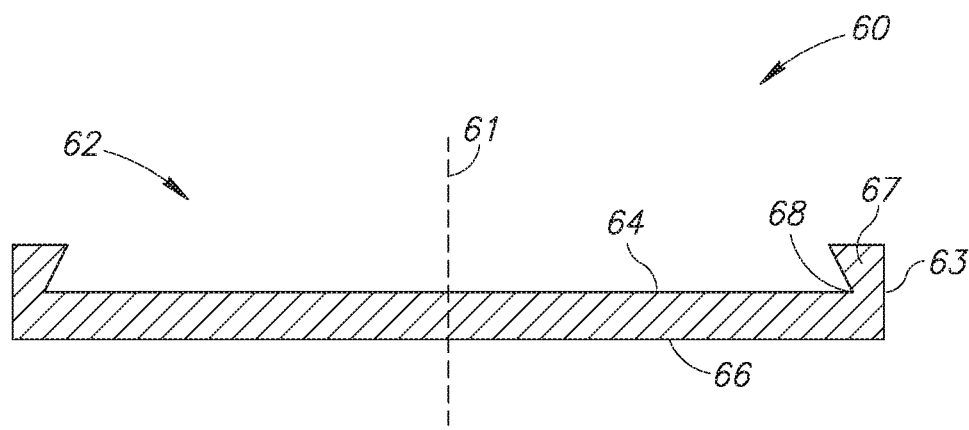
FIG. 7 is a transverse cross section of the discrete base member along line 7-7 in FIG. 6.
Figure 8:
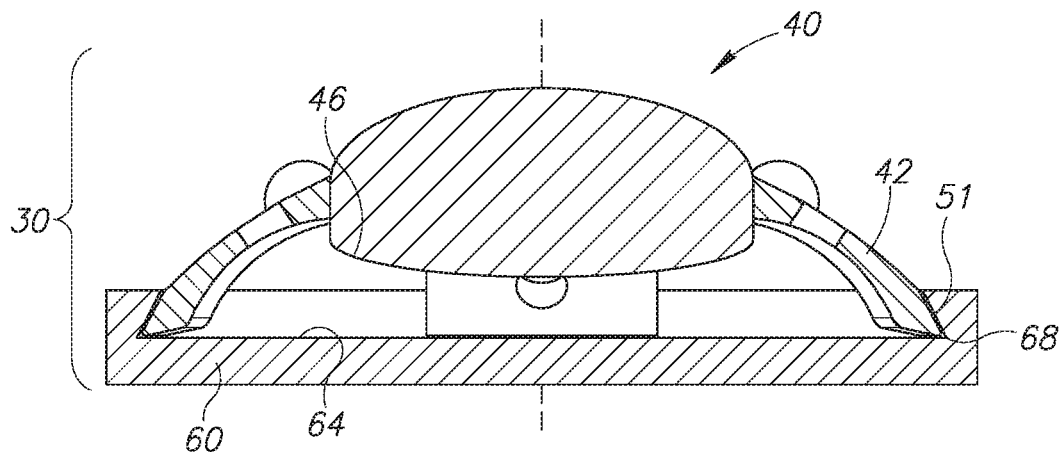
FIG. 8 is a transverse cross section of an in-the-hand assembled hybrid AIOL assemblage.

FIG. 6 and FIG. 7 show the discrete base member 60 has a flat circular base member centerpiece 62 having a flat circular anterior base member centerpiece surface 64 and a flat circular posterior base member centerpiece surface 66. The flat anterior and posterior base member centerpiece surfaces 64 and 66 have zero optical power. The base member surround 63 is formed with an elevated circumferential retainer 67 for forming a circumferential groove 68 with the anterior base member centerpiece surface 64 for receiving the lens haptics free ends 51 for anchoring the discrete lens unit 40 on the discrete base member 60. The base member surround 63 preferably has a square cross section for preventing the migration of epithelial cells from a capsular periphery. FIG. 8 shows the assembled hybrid AIOL assemblage 30 on mounting the lens unit 40 on the base member 60 by means of the lens haptics free ends 51 being flexed into the circumferential groove 68 such that the lens haptics 42 urge the posterior lens optics surface 46 away from the anterior base member centerpiece surface 64.

Figure 9:
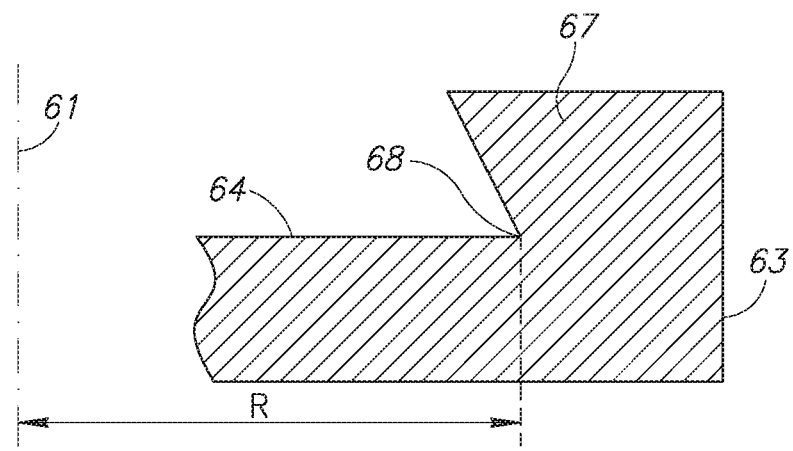
FIG. 9 is a transverse cross section of an edge of another discrete base member.
Figure 10:
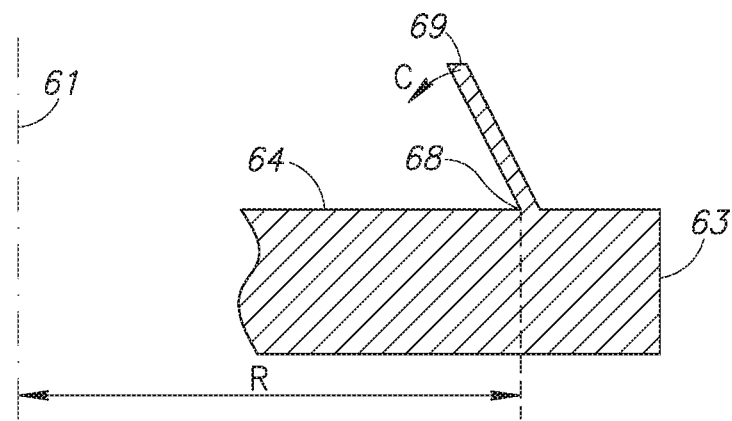
FIG. 10 is a transverse cross section of an edge of yet another discrete base member.

Capsular bag size can vary by several millimeters. The hybrid AIOL assemblages 30 are designed such that the same discrete lens unit 40 can be implanted in different sized human capsular bags. This is achieved by the provision of discrete base members 60 having their circumferential groove 68 at the same radius R relative to the base member centerline 61 and compensating for capsular size differences by radial outward extending of the base member surround 63 and the elevated circumferential retainer 67 as can be seen on comparison of FIG. 9 to FIG. 7. FIG. 10 shows an alternative elevated circumferential retainer 67 in the form of a pliable rim 69 designed to be flexed towards the anterior base member centerpiece surface 64 by the anterior capsule flange 27 as denoted by arrow C to improve the mechanical interface between the anterior capsule flange 27 and the lens haptics 42. The pliable rim 69 is deployed at the same radius R from the base member centerline 61 and capsular size differences are compensated by radial outward extending of the base member surround 63 with respect to the base member centerline 61.

Figure 1:
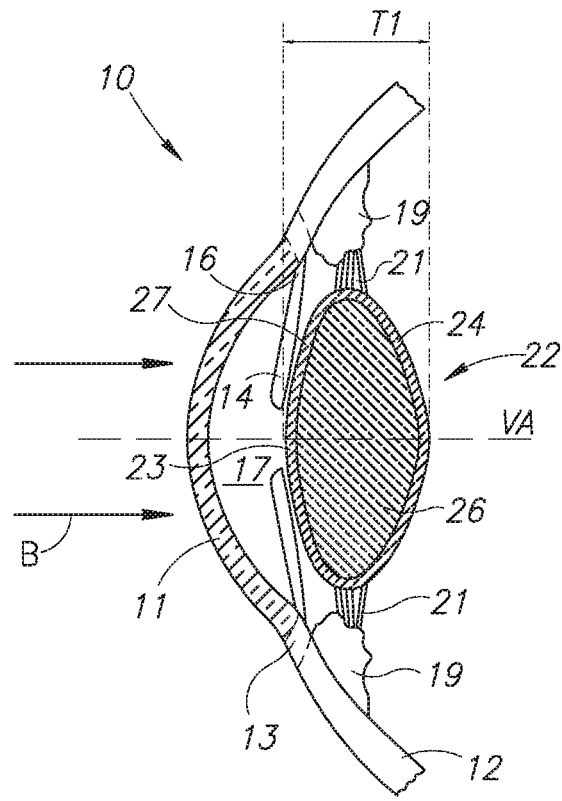
FIG. 1 is a cross section of an anterior part of a human eye in its natural near vision condition in an axial plane of the human body.
Figure 11:
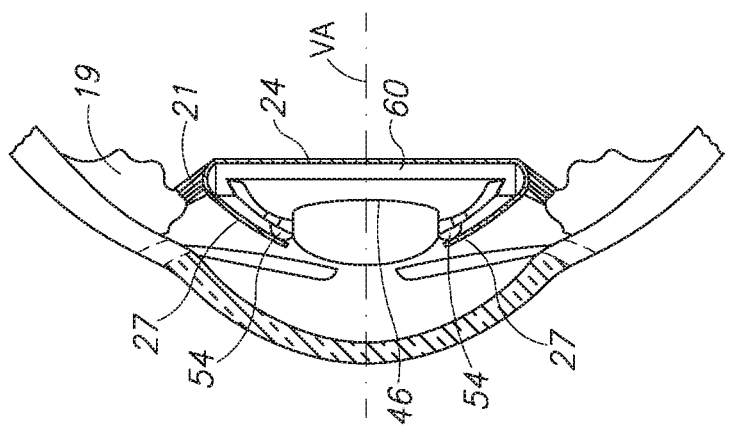
FIG. 11 is a cross section of an implanted hybrid AIOL assemblage for near vision corresponding to FIG. 1.

FIG. 11 show an implanted hybrid AIOL assemblage 30 in an operative near vision state corresponding to FIG. 1. Full ciliary body contraction is accompanied by iris contraction to about 2.5 mm diameter pupil size. FIG. 11 shows the anterior capsule flange 27 contacting the anterior lens optics surface 44 and/or the haptics spacers 54 but not urging the lens optics 41 towards the base member centerpiece 62 such that the posterior lens optics surface 46 is spaced apart from the anterior base member centerpiece surface 64. Accordingly, the hybrid AIOL assemblage 30 affords the combined optical power of the anterior lens optics surface 44 and the central circle 48's optical power to enable near vision.

Figure 2:
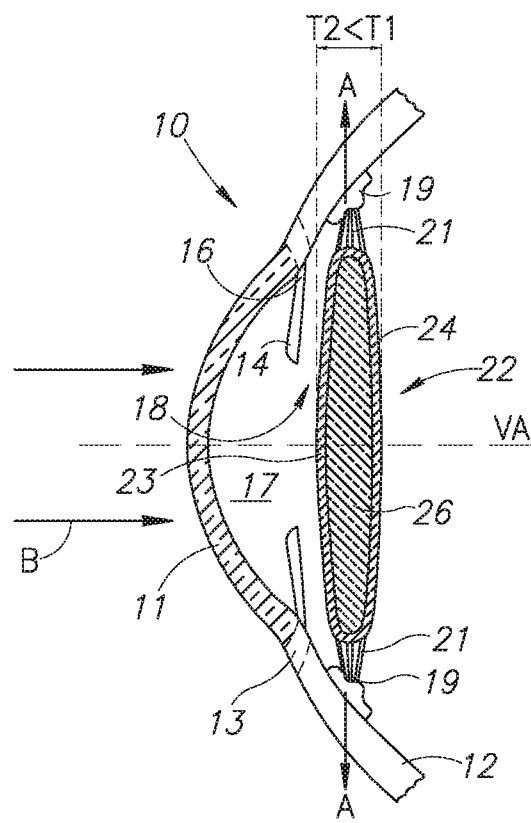
FIG. 2 is a cross section of an anterior part of a human eye in its natural distance vision condition in an axial plane of the human body.
Figure 12:
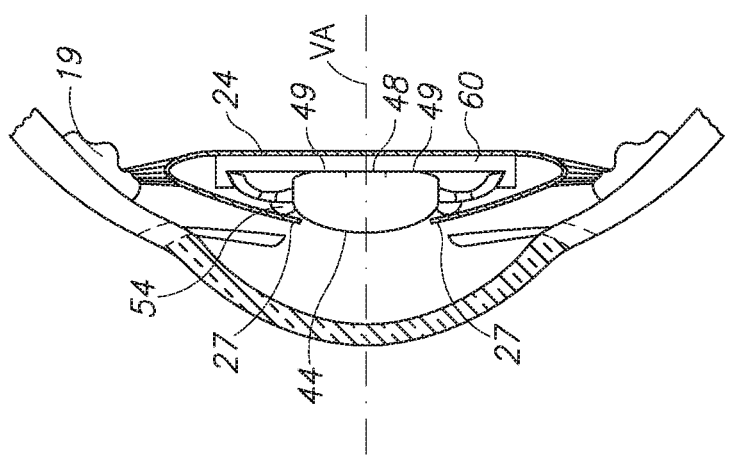
FIG. 12 is a cross section of the implanted hybrid AIOL assemblage for distance vision corresponding to FIG. 2.

FIG. 12 shows the implanted hybrid AIOL assemblage 30 in an operative distance vision state corresponding to FIG. 2. FIG. 12 shows the anterior capsule flange 27 pressing down on the anterior lens optics surface 44 and/or the haptics spacers 54 for urging the lens optics 41 towards the base member centerpiece 62. The posterior lens optics surface 46 is entirely intimately immerged in the anterior base member centerpiece surface 64 such that the posterior lens optics surface 46 and the anterior base member centerpiece surface 64 create a single refractive index optical continuum of zero optical power whereby the hybrid AIOL assemblage 30 affords optical power by virtue of the anterior lens optics surface 44 suitably determined for best distance vision of an intended implanted eye.

Figure 13:
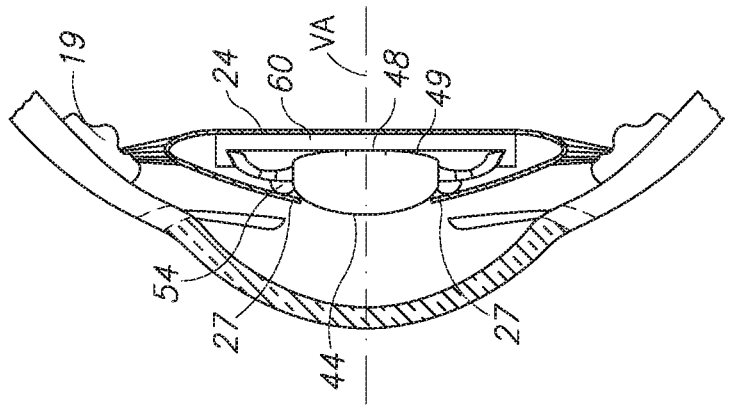
FIG. 13 is a cross section of the implanted hybrid AIOL assemblage for intermediate vision.

FIG. 13 shows the implanted hybrid AIOL assemblage 30 in an operative intermediate vision state. The intermediate vision involves a ciliary body contraction much smaller than for near vision leading to the posterior lens optics surface 46 being partially intimately immerged in the anterior base member centerline surface 64. As shown, only the central circle 48 and the anterior base member centerpiece surface 64 create a single refractive index optical continuum of zero optical power. The annular multi-focal segment 49 is spaced apart from the anterior base member centerpiece surface 64 thereby affording the required additional optical power for intermediate vision.

While the invention has been described with respect to a limited number of embodiments, it will be appreciated that many variations, modifications, and other applications of the invention can be made within the scope of the appended claims.

The invention claimed is:

1. A hybrid accommodating intraocular lens assemblage for implantation in a post-capsulorhexis human eye having a visual axis, an annular ciliary body, and a vacated capsular bag having an annular anterior capsule flange and an intact posterior capsule, the ciliary body having a relaxed ciliary body state for distance vision and a contracted ciliary body state for near vision, the ciliary body peripherally tensioning the capsular bag on its relaxation from its contracted ciliary body state to its relaxed ciliary body state, the hybrid accommodating intraocular lens assemblage comprising:

(a) a discrete base member having a base member centerline and including a flat circular base member centerpiece and a peripheral base member surround, said flat circular base member centerpiece having a base member centerpiece refractive index, an anterior base member centerpiece surface and a posterior base member centerpiece surface, said base member having an elevated circumferential retainer bounding a circumferential groove with said anterior base member centerpiece surface; and (b) a discrete lens unit having i) a lens optic having a lens optic refractive index, a lens optic axis for co-axial alignment with the visual axis, an anterior lens optic surface with a primary optical power for distance vision and a posterior lens optic surface having a central circle with an additional optical power to said primary optical power for near vision, and ii) at least two spaced apart resiliently flexible lens haptics radially extending from said lens optic for insertion in said circumferential groove for anchoring said discrete lens unit on said discrete base member for urging said lens optic away from said discrete base member for separating said posterior lens optic surface from said anterior base member centerpiece surface, said at least two spaced apart resiliently flexible lens haptics each having a free end remote from said lens optic, said elevated circumferential retainer being configured to overlie said free ends for anchoring said discrete lens optic on said discrete base member, and enabling rotation of said discrete lens unit to a predetermined position relative to said discrete base member stationary in the post-capsulorhexis human eye, and wherein said base member centerpiece and said lens optic have the same refractive index, and whereupon, pursuant to an initial implantation of said discrete base member in the vacated capsular bag and a subsequent implantation of said discrete lens unit in the vacated capsular bag between said base member and the anterior capsule flange, in the relaxed ciliary body state, the vacated capsular bag urges said lens optic and said base member towards each other such that said posterior lens optic surface is intimately immerged in said anterior base member centerpiece surface for creating a single refractive index optical continuum nullifying said posterior lens optic surface's optical power whereby the hybrid accommodating intraocular lens assemblage has optical power for distance vision only, and in the contracted ciliary body state, the vacated capsular bag enables said at least two spaced apart resiliently flexible lens haptics to space apart said lens optic and said base member such that said posterior lens optic surface is spaced apart from said anterior base member centerpiece surface for adding said central circle's additional optical power to said anterior lens optic surface's primary optical power whereby the hybrid accommodating intraocular lens assemblage has a combined optical power for near vision.

2. The assemblage according to claim 1 wherein said posterior lens optic surface includes an annular multi-focal segment surrounding said central circle with a gradual decreasing optical power from said lens optic axis towards said at least two spaced apart resiliently flexible lens haptics for intermediate vision correction, whereupon, in an intermediate ciliary body state between the relaxed ciliary body state and the contracted ciliary body state, said central circle is intimately immerged in said anterior base member centerpiece surface for creating a single refractive index optical continuum nullifying said central circle's optical power and said annular multi-focal segment is spaced apart from said anterior base member centerpiece surface for intermediate vision.

3. The assemblage according to claim 1 wherein said posterior lens optics surface is a mono-focal lens optics surface from said lens optics axis to said at least two spaced apart resiliently flexible lens haptics.

4. The assemblage according to claim 1 wherein each lens haptics of said at least two lens haptics includes at least one anterior spacer for spacing the anterior capsule flange therefrom on said subsequent implantation of said discrete lens unit in the vacated capsular bag.

5. The assemblage according to claim 1 wherein said peripheral base member surround has a square cross section in a transverse cross section.

6. The assemblage according to claim 1 wherein said elevated circumferential retainer is constituted by a pliable rim.

7. The assemblage according to claim 1 wherein said anterior lens optic surface is combined with a toric optical design for correction of astigmatism, and said discrete lens unit includes an optical axis marker for assisting alignment of said discrete lens unit relative to the visual axis during implantation of said discrete lens unit.

\* \* \* \* \*